United States Patent [19]

Zuk et al.

[11] 4,281,061

[45] Jul. 28, 1981

[54] DOUBLE ANTIBODY FOR ENHANCED SENSITIVITY IN IMMUNOASSAY

[75] Inventors: Robert F. Zuk, San Francisco; Ian Gibbons, Menlo Park; Gerald L. Rowley, Cupertino; Edwin F. Ullman, Atherton, all of Calif.

[73] Assignee: Syva Company, Palo Alto, Calif.

[21] Appl. No.: 61,542

[22] Filed: Jul. 27, 1979

[51] Int. Cl.$^3$ .................... C12N 9/96; G01N 33/54; G01N 33/48; G01N 31/14

[52] U.S. Cl. ............................. 435/7; 435/5; 435/188; 424/8; 424/12; 23/230 B

[58] Field of Search .................... 424/8, 12; 23/230 B; 435/5, 7, 184, 188, 810

[56] References Cited

U.S. PATENT DOCUMENTS

| | | | |
|---|---|---|---|
| 3,935,074 | 1/1976 | Rubenstein | 424/12 X |
| 3,966,898 | 6/1976 | Sjöquist et al. | 435/7 |
| 4,161,515 | 7/1979 | Ullman | 424/8 |
| 4,189,466 | 2/1980 | Ainis et al. | 23/230 B |
| 4,193,983 | 3/1980 | Ullman et al. | 435/7 |

*Primary Examiner*—Thomas G. Wiseman
*Attorney, Agent, or Firm*—Bertram I. Rowland

[57] ABSTRACT

Method and compositions are provided for performing homogeneous immunoassays. The method involves having a signal producing system, which provides a detectable signal, which system includes a macromolecular member. The determination of the analyte, which is a member of a specific binding pair consisting of a ligand and its homologous receptor, is performed by creating an extensive matrix in the assay medium by having in the assay medium in addition to the analyte, ligand labeled with one of the members of the signal producing system, antiligand either present as the analyte or added, a polyvalent receptor for antiligand, the macromolecular member of the signal producing system, and any additional members of the signal producing system. The labeled ligand, antiligand, and polyvalent receptor for the antiligand create a matrix which modulates, e.g. inhibits, the approach of the macromolecular member of the signal producing system to the labeled ligand. The extent and degree of formation of the matrix is dependent upon the concentration of the analyte in the medium. By comparing the signal from an assay medium having an unknown amount of analyte, with a signal obtained from an assay medium having a known amount of analyte, the amount of analyte in the unknown sample may be determined qualitatively or quantitatively.

Kits are provided having predetermined amounts of the various reagents to allow for enhanced sensitivity of the method.

17 Claims, No Drawings

DOUBLE ANTIBODY FOR ENHANCED SENSITIVITY IN IMMUNOASSAY

BACKGROUND OF THE INVENTION

1. Field of the Invention

There is a continuing and increasing need for accurate, sensitive techniques for measuring trace amounts of organic materials in a wide variety of samples. This need includes the measurement of drugs, naturally occurring physiologically active compounds or nutrients in physiological fluids, the presence of trace amounts of contaminants or toxic materials in foods, water or other fluids, and the like, as well as monitoring materials for trace contamination introduced during chemical processing.

Among the various techniques which have found increasing exploration are techniques involving receptors which recognize or bind to a specific polar and spatial organization of one or more molecules. For the most part, the receptors are antibodies and the techniques are referred to as immunoassays. These techniques conventionally employ a labeled ligand where the binding to the receptor allows for distinguishing between a bound labeled ligand and an unbound labeled ligand. Certain techniques, generally referred to as heterogeneous, rely on segregating the bound from the unbound labeled ligand. Other techniques, generally referred to as homogeneous, rely on the bound labeled ligand providing a signal level different from unbound labeled ligand.

In many of the homogeneous techniques, the label must interact with another substance in order to differentiate the signal. For example, in one technique, the label is an enzyme and when receptor is bound to the ligand the enzymatic activity is inhibited. This requires that the enzyme ligand combination be such that when receptor is bound to the enzyme ligand conjugate, either substrate is inhibited from entering the active site or the enzyme is allosterically modified, so that its turnover rate is substantially reduced. In another technique, a fluorescent label is employed in conjunction with a receptor for the fluorescer. The binding of the receptor to the fluorescer substantially diminishes the fluorescence when the fluorescer is irradiated with light which normally excites the fluorescer. When the fluorescer is conjugated to ligand, and antiligand is bound to the conjugate, the antifluorescer is inhibited from binding to the fluorescer.

While these techniques have found great use or show great promise, there is still an interest in enhancing the sensitivity of techniques which do not require separation. As lower and lower concentrations of analytes are encountered, improvements in available techniques are required to allow for accurate determination of the presence of extremely small amounts of the analyte. Therefore, there has been an ongoing effort to find new and improved ways to measure extremely small amounts of organic molecules in a wide variety of environments.

2. Description of the Prior Art

U.S. Pat. No. 3,817,837 describes a homogeneous enzyme immunoassay. U.S. Pat. No. 3,996,345 describes a homogeneous immunoassay employing two chromophores related by being a fluorescer and a quencher. Co-pending application Ser. No. 893,650, filed Apr. 5, 1978 describes a technique employing a plurality of enzymes, where the substrate of one enzyme is the product of the other enzyme. U.S. Pat. No. 3,935,074 describes an immunoassay involving steric hindrance between two antibodies. Co-pending application Ser. No. 815,487, describes an enzyme immunoassay, employing antienzyme as an inhibitor.

SUMMARY OF THE INVENTION

Method and compositions are provided for enhancing the sensitivity of immunoassays requiring the proximity of two reagents for modulating a signal related to the amount of analyte in the assay medium. The subject method employs a second receptor, which is polyvalent, and binds to a receptor for ligand to affect the degree of interaction between the two reagents, particularly inhibiting interaction. The role of the second receptor is manifold depending upon the nature of the two reagents involved in signal production. The second receptor is employed in forming or extending matrices of ligand and ligand receptor which results in modulation of entry or exit from the matrix. Depending upon the role of the second receptor, different protocols will be employed.

A kit is provided having predetermined amounts of the various reagents, as well as ancillary reagents for optimizing the sensitivity of the immunoassay.

DESCRIPTION OF THE SPECIFIC EMBODIMENTS

Method and composition are provided for determining small amounts of organic compounds in a wide variety of media by employing an organic receptor which recognizes a specific spatial and polar organization of a molecule, either the organic compound or its receptor being the analyte of interest. In the subject method, a signal producing system is employed having at least two members which provides a detectible signal which may be modulated in accordance with the concentration of the analyte in the assay medium. The modulation of the signal is as a result of two members of the signal producing system being brought into proximity, which results in either an enhancement or reduction in the signal level. Two receptors are involved in the assay: the first receptor, which is added when the organic compound or ligand is the analyte, or is inherently present when the first receptor is the analyte; and a second receptor, which is polyvalent and specifically binds to the first receptor. The presence of the second receptor enhances the differentiation in signal level as a result of the degree of proximity of the two reagents of the signal producing system.

In the broadest sense in performing the assay, the analyte, which is a member of a specific binding pair—ligand and its homologous receptor—is introduced into an assay medium in combination with: (1) antiligand, when ligand is the analyte; (2) ligand conjugated to a label, where the label is a member of a signal producing system; (3) a second member of the signal producing system which interacts with the first member to modulate the signal depending on the proximity of the second member of the signal producing system to the first member of the signal producing system; (4) a polyvalent receptor for the antiligand; (5) and any ancillary reagents necessary for the signal producing system. Depending upon the particular signal producing system, various protocols will be employed.

By modulation is intended to create, destroy, modify, affect or change the signal, so as to allow a detectable difference by virtue of the interaction of the label and macromolecular reagent.

Definitions

Analyte—the compound or composition to be measured, which may be a ligand, which is mono- or polyepitopic (antigenic determinants) or haptenic, a single or plurality of compounds which share at least one common epitopic site, or a receptor capable of binding to a specific polar or spatial organization.

Specific binding pair—two different molecules, where one of the molecules has an area on the surface or in a cavity which specifically binds to a particular spatial and polar organization of the other molecule. The members of the specific binding pair are referred to as ligand and receptor (antiligand).

Ligand—any organic compound for which a receptor naturally exists or can be prepared.

Receptor—any compound or composition capable of recognizing a particular spatial and polar organization of a molecule i.e. epitopic site. Illustrative receptors include naturally occurring receptors, e.g. thyroxine binding globulin, antibodies, enzymes, Fab fragments, lectins, and the like.

In the subject invention, a polyvalent receptor, normally an antibody, for the ligand receptor anti(antiligand) will be employed. The anti(antiligand) is prepared by employing the antiligand as an immunogen in a vertebrate different from the source of the antiligand.

Signal Producing System—the signal producing system will have at least two components, at least one component being conjugated to ligand and another component which will be a macromolecular reagent. The signal producing system produces a measurable signal which is detectible by external means, usually the measurement of electromagnetic radiation. For the most part, the signal producing system will involve enzymes, antibodies, and chromophores, where chromophores include dyes which absorb light in the ultraviolet or visible region, fluorescers, phosphors and chemiluminescers. While for the most part, the signal is conveniently the absorption or emission of electromagnetic radiation, usually in the ultraviolet or visible range, electrochemical changes, thermal changes, nephelometric, and the like may also find application. The subject signal producing system requires that the macromolecular reagent interact with or react with, directly or indirectly, the member of the signal producing system (label) bound to the ligand, resulting in the production, enhancement or diminution of the signal observed for the label.

Macromolecular reagent—the macromolecular reagent is a member of the signal producing system, which reacts or interacts with, directly or indirectly, the member of the signal producing system bound to the ligand, so as to modulate the signal produced by the label. The macromolecular reagent will be at least $1 \times 10^4$, usually at least $5 \times 10^4$ molecular weight, and preferably greater than $1 \times 10^5$ molecular weight, and may be 10 million molecular weight or more. The macromolecular reagent may be a single compound, a group of compounds, covalently or noncovalently linked together, or one or a plurality, usually a plurality, of molecules bound to a hub nucleus. The hub nucleus may be water soluble or insoluble, and is a polyfunctional material, normally polymeric, having a plurality of functional groups, such as hydroxy, amino, mercapto, ethylenic, etc., as sites for linking. The hub nucleus will generally have a molecular weight equal to or greater than 10,000, usually 50,000 molecular weight. Illustrative hub nucleii include polysaccharides, polypeptides, including proteins, nucleic acids, ion exchange resins, vinyl polymers, such as polyacrylamides and vinyl alcohols, polyethers, polyesters, and the like. The significant factor of the macromolecular reagent is that its approach to the label bonded to the ligand will be affected, when a large immunological matrix is formed by polyvalent receptors about the labeled ligand associated with antiligand.

Ligand-receptor matrix—the matrix is a matrix formed from a plurality of ligands, ligand receptors, and antireceptors, where at least the antireceptors are polyvalent, and normally all the members of the matrix are polyvalent. What is intended is that a plurality of ligands, which are bound to ligand receptors, are connected by a plurality of bridges formed by antireceptors, which results in relatively large reticulated microstructures, capable of modulating, usually reducing, the rate of diffusion of a molecule in the environment of the matrix up to and including steric exclusion.

Labeled Ligand—the conjugate of the ligand member of the specific binding pair covalently bonded to a member of the signal producing system, either joined by a bond, linking group or hub nucleus. The labeled ligand may have one or more ligands or one or more labels or a plurality of both. Where conjugation of the label and ligand are required, the ligand will normally be modified to provide for a site for linking. The modified ligand is referred to as ligand analog, and the ligand analog may differ from the ligand by replacement of a hydrogen or more usually by the introduction of or modification of a functional group.

Poly(ligand analog)—a plurality of haptenic ligand analogs bonded to a water soluble hub nucleus of at least about 10,000 molecular weight, usually 30,000 to 600,000, e.g. proteins, polysaccharides, nucleic acids, synthetic polymers, etc.

Method

The subject assay is carried out in an aqueous zone at a moderate pH, generally close to optimum assay sensitivity, without separation of the assay components or products. The assay zone for the determination of analyte is prepared by employing an appropriate aqueous medium, normally buffered, the unknown sample which may have been subject to prior treatment, the labeled ligand, ligand receptor (antiligand), the macromolecular reagent member of the signal producing system, and antireceptor as well as any additional materials required for the signal producing system for producing a detectible signal. In the event that antiligand is the analyte, antiligand need not be added.

The presence of ligand or its homologous receptor (antiligand) in the unknown will affect the extent to which the macromolecular reagent interacts with the labeled ligand.

In carrying out the assay, an aqueous medium will normally be employed. Other polar solvents may also be included, usually oxygenated organic solvents from one to six, more usually from one to four carbon atoms, including alcohols, ethers and the like. Usually these cosolvents will be present in less than about 40 weight percent, more usually in less than about 20 weight percent.

The pH for the medium will usually be in the range of about 4 to 11, more usually in the range of about five to ten, and preferably in the range of about 6.5–9.5. The pH is chosen so as to maintain a significant level of specific binding by the receptor while optimizing signal producing efficiency. In some instances, a compromise will be made between these two considerations. Various buffers may be used to achieve the desired pH and maintain the pH during the determination. Illustrative buffers include borate, phosphate, carbonate, tris, barbital, and the like. The particular buffer employed is not critical to this invention, but in individual assays one buffer may be preferred over another.

Moderate temperatures are normally employed for carrying out the assay and usually constant temperatures during the period of the measurement, particularly for rate determinations. The temperatures for the determination will generally range from about 10° to 50° C., more usually from about 15° to 40° C.

The concentration of analyte which may be assayed will generally vary from about $10^{-4}$ to $10^{-15}$M, more usually from about $10^{-6}$ to $10^{-13}$M. Considerations such as whether the assay is qualitative, semiquantitative or quantitative, the particular detection technique and the concentration of the analyte of interest will normally determine the concentration of the other reagents.

While the concentrations of the various reagents in the assay medium will generally be determined by the concentration range of interest of the analyte, the final concentration of each of the reagents will normally be determined empirically to optimize the sensitivity of the assay over the range of interest. The total binding sites of the members of the specific binding pair which are reciprocal to the analyte will be not less than about 0.1 times the minimum concentration of interest based on binding sites of analyte and usually not more than about 1,000 times the maximum concentration of interest based on analyte binding sites, usually about 0.1 to 100 times, more usually about 0.3 to 10 times the maximum concentration of interest. By concentration is intended the available concentration, that is, the concentration at saturation and not necessarily the actual concentration where all members of the specific binding pair may not be equally available for binding.

Depending upon the particular signal producing system, as well as the manner in which the specific binding pair members are employed, the amount of the various members of the signal producing system can be varied relatively widely. That is, relatively large excesses of the macromolecular reagent may be employed, where either the rate of formation of the matrix is high as compared to the interaction between the label and the macromolecular reagent or the matrix is allowed to form initially, followed by introduction of the macromolecular reagent. As suggested above, the order of addition of the various reagents may vary widely, depending on the particular label and signal producing system, the nature of the analyte, the relative concentrations of analyte and reagents, the mode of determination, and the sensitivity desired.

When ligand is the analyte, the addition of ligand will normally diminish complex formation involving labeled ligand, so that the interaction between the labeled ligand and the macromolecular reagent will be enhanced with increasing amounts of ligand being present in the assay medium. By contrast, when ligand receptor is the analyte, there can be no complex formation in the absence of ligand.

For ligand analyte, conveniently the ligand may be combined with antiligand, so that available binding sites of the antiligand become filled by the available ligand. To the extent that ligand is present, the amount of antiligand available for binding labeled ligand will be reduced. Alternative ways would be to combine both the ligand and labeled ligand simultaneously with the antiligand, but one would normally not combine the labeled ligand with the antiligand prior to addition of the ligand analyte. This is due to the fact that with many receptors, the association of the specific binding pair members is almost irreversible during the time period of an assay.

While for the most part, ligand analytes will be antigens, which have a plurality of determinant (epitopic) sites, haptenic (mono-epitopic) compounds can also be employed by having a plurality of haptens conjugated to a large label (often greater than 10,000, usually greater than 30,000 molecular weight) or a plurality of haptens and labels bonded to a water soluble hub nucleus.

One or more incubation steps may be involved in preparing the assay medium. For example, it will usually be desirable to incubate an antigen analyte with the antiligand. In addition, it may be desirable to have a second incubation after addition of the antireceptor. Whether to employ an incubation period and the length of the incubation period will depend to a substantial degree on the mode of determination—rate or equilibrium—and the rate of binding of the receptors to their homologous members. Usually, incubation steps will vary from about 0.5 min to 6 hrs, more usually from about 5 min to 1 hr. Incubation temperatures will generally range from about 4° to 50° C., more usually from about 15° to 37° C.

After the reagents are combined the signal will then be determined. The method of determination may be the observation of electromagnetic radiation, particularly ultraviolet and visible light, either absorption or emission, calorimetric, electrochemical, nephelometric, or the like. Desirably, the signal will be read as electromagnetic radiation in the ultraviolet or visible region, particularly from about 250 to 750 nm, usually from about 350 to 650 nm.

The temperature at which the signal is observed will generally range from about 10° to 50° C., more usually from about 15° to 40° C.

Standard assay media can be prepared which have known amounts of the analyte. The observed signal for the standard assay media may then be plotted, so as to relate concentration to signal level. Once a standard curve has been established, a signal level may be directly related to the concentration of the analyte.

The time for measuring the signal will vary depending on whether a rate or equilibrium mode is used, the sensitivity required, the nature of the signal producing system and the like. For rate modes, the times between readings will generally range from about 5 sec to 6 hrs, usually about 10 sec to 1 hr. For the equilibrium mode, after a steady state is achieved, a single reading may be sufficient or two readings over any convenient time interval may suffice.

For the most part, the labels bound to the ligand will be catalysts, particularly enzymes or oxidation-reduction catalysts, chromogens, which absorb or emit light in the ultraviolet or visible region, such as dyes, fluorescers, chemiluminescers, donor-acceptor fluorescer combinations, phosphorescers, or enzyme binding substances e.g. chromogenic substrates, cofactors and inhibitors, and the like.

Materials

The components employed in the assay will be the labeled ligand, antiligand when ligand is the analyte, macromolecular reagent, and receptor for the ligand receptor, anti(antiligand), as well as any additional members of the signal producing system.

Analyte

The ligand analytes of this invention are characterized by being monoepitopic or polyepitopic. The polyepitopic ligand analytes will normally be poly(amino acids) i.e. polypeptides and proteins, polysaccharides, nucleic acids, and combinations thereof. Such combinations of assemblages include bacteria, viruses, chromosomes, genes, mitochondria, nuclei, cell membranes, and the like.

For the most part, the polyepitopic ligand analytes employed in the subject invention will have a molecular weight of at least about 5,000, more usually at least about 10,000. In the poly(amino acid) category, the poly(amino acids) of interest will generally be from about 5,000 to 5,000,000 molecular weight, more usually from about 20,000 to 1,000,000 molecular weight; among the hormones of interest, the molecular weights will usually range from about 5,000 to 60,000 molecular weight.

The wide variety of proteins may be considered as to the family of proteins having similar structural features, proteins having particular biological functions, proteins related to specific microorganisms, particularly disease causing microorganisms, etc.

The following are classes of proteins related by structure:

protamines
histones
albumins
globulins
scleroproteins
phosphoproteins
mucoproteins
chromoproteins
lipoproteins
nucleoproteins
glycoproteins
proteoglycans
unclassified proteins, e.g. somatotropin, prolactin, insulin, pepsin A number of proteins found in the human plasma are important clinically and include:

Prealbumin
Albumin
$\alpha_1$-Lipoprotein
$\alpha_1$-Acid glycoprotein
$\alpha_1$-Antitrypsin
$\alpha_1$-Glycoprotein
Transcortin
4.6S-Postalbumin
Tryptophan-poor
   $\alpha_1$-glycoprotein
$\alpha_1\chi$-Glycoprotein
Thyroxin-binding globulin
Inter-$\alpha$-trypsin-inhibitor
Gc-globulin
  (Gc 1-1)
  (Gc 2-1)
  (Gc2-4 2)
Haptoglobin
  (Hp 1-1)
  (Hp 2-1)
  (Hp 2-4 2)
Ceruloplasmin
Cholinesterase
$\alpha_2$-Lipoprotein(s)
Myoglobin
C-Reactive Protein
$\alpha_2$-Macroglobulin
$\alpha_2$-HS-glycoprotein
Zn-$\alpha_2$-glycoprotein
$\alpha_2$-Neuramino-glycoprotein
Erythropoietin
$\beta$-lipoprotein
Transferrin
Hemopexin
Fibrinogen
Plasminogen
$\beta_2$-glycoprotein I
$\beta_2$-glycoprotein II
Immunoglobulin G
  (IgG) or $\gamma$G-globulin
Mol. formula:
  $\gamma_2\kappa_2$ or $\gamma_2\lambda_2$
Immunoglobulin A (IgA) or $\gamma$A-globulin
Mol. formula:
  $(\alpha_2\kappa_2)^n$ or $(\alpha_2\lambda_2)^n$
Immunoglobulin M
  (IgM) or $\gamma$M-globulin
Mol. formula:
  $(\mu_2\kappa_2)^5$ or $(\mu_2\lambda_2)^5$
Immunoglobulin D(IgD) or $\gamma$D-Globulin ($\gamma$D)
Mol. formula:
  $(\delta_2\kappa_2)$ or $\delta_2\lambda_2)$
Immunoglobulin E (IgE) or $\gamma$E-Globulin ($\gamma$E)
Mol. formula:
  $(\epsilon_2\kappa_2)$ or $(\epsilon_2\lambda_2)$
Free $\kappa$ and $\lambda$ light chains
Complement factors:
C'1
  C'1q
  C'1r
  C'1s
C'2
C'3
  $\beta_1$A $\alpha_2$D
C'4
C'5
C'6
C'7
C'8
C'9

Important blood clotting factors include:

| BLOCK CLOTTING FACTORS | |
|---|---|
| International designation | Name |
| I | Fibrinogen |
| II | Prothrombin |
| IIa | Thrombin |
| III | Tissue thromboplastin |
| V and VI | Proaccelerin, accelerator globulin |
| VII | Proconvertin |
| VIII | Antihemophilic globulin (AHG) |
| IX | Christmas factor, plasma thromboplastin component (PTC) |
| X | Stuart-Prower factor, autoprothrombin III |

BLOOD CLOTTING FACTORS

| International designation | Name |
|---|---|
| XI | Plasma thromboplastin antecedent (PTA) |
| XII | Hagemann factor |
| XIII | Fibrin-stabilizing factor |

Important protein hormones include:

Peptide and Protein Hormones

Parathyroid hormone (parathromone)
Thyrocalcitonin
Insulin
Glucagon
Relaxin
Erythropoietin
Melanotropin (melanocyte-stimulating hormone; intermedin)
Somatotropin (growth hormone)
Corticotropin (adrenocorticotropic hormone)
Thyrotropin
Follicle-stimulating hormone
Luteinizing hormone (interstitial cell-stimulating hormone)
Luteomammotropic hormone (luteotropin, prolactin)
Gonadotropin (chorionic gonadotropin)

Tissue Hormones

Secretin
Gastrin
Angiotensin I and II
Bradykinin
Human placental lactogen

Peptide Hormones from the Neurohypophysis

Oxytocin
Vasopressin
Releasing factors (RF) CRF, LRF, TRF, Somatotropin-RF, GRF, FSH-RF, PIF, MIF Other polymeric materials of interest are mucopolysaccharides and polysaccharides.

Illustrative antigenic polysaccharides derived from microorganisms are as follows:

| Species of Microorganisms | Hemosensitin Found in |
|---|---|
| Streptococcus pyogenes | Polysaccharide |
| Diplococcus pneumoniae | Polysaccharide |
| Neisseria meningitidis | Polysaccharide |
| Neisseria gonorrheae | Polysaccharide |
| Corynebacterium diphtheriae | Polysaccharide |
| Actinobacillus mallei; Actinobacillus whitemori | Crude extract |
| Francisella tularensis | Lipopolysaccharide |
| Pasteurella pestis | Polysaccharide |
| Pasteurella pestis | Polysaccharide |
| Pasteurella multocida | Capsular antigen |
| Brucella abortus | Crude extract |
| Haemophilus influenzae | Polysaccharide |
| Haemophilus pertussis | Crude |
| Treponema reiteri | Polysaccharide |
| Veillonella | Lipopolysaccharide |
| Erysipelothrix | Polysaccharide |
| Listeria monocytogenes | Polysaccharide |
| Chromobacterium | Lipopolysaccharide |
| Mycobacterium tuberculosis | Saline extract of 90% phenol extracted mycobacteria and polysaccharide fraction of cells and turberculin |
| Klebsiella aerogenes | Polysaccharide |
| Klebsiella cloacae | Polysaccharide |
| Salmonella typhosa | Lipopolysaccharide, Polysaccharide |
| Salmonella typhi-murium; Salmonella derby Salmonella pullorum | Polysaccharide |
| Shigella dysenteriae | Polysaccharide |
| Shigella flexneri | |
| Shigella sonnei | Crude, Polysaccharide |
| Rickettsiae | Crude extract |
| Candida albicans | Polysaccharide |
| Entamoeba histolytica | Crude extract |

The microorganisms which are assayed may be intact, lysed, ground or otherwise fragmented, and the resulting composition or portion, e.g. by extraction, assayed. Microorganisms of interest include:

Corynebacteria
Corynebacterium diptheriae
Pneumococci
Diplococcus pneumoniae
Streptococci
Streptococcus pyogenes
Streptococcus salivarus
Staphylococci
Staphylococcus aureus
Staphylococcus albus
Neisseriae
Neisseria meningitidis
Neisseria gonorrheae
Enterobacteriaciae

| | |
|---|---|
| Escherichia coli<br>Aerobacter aerogenes<br>Klebsiella pneumoniae | } The coliform bacteria |
| Salmonella typhosa<br>Salmonella choleraesuis<br>Salmonella typhimurium | } The Salmonellae |
| Shigella dysenteriae<br>Shigella schmitzii<br>Shigella arabinotarda<br>Shigella flexneri<br>Shigella boydii<br>Shigella Sonnei | } The Shigellae |

Other enteric bacilli

| | |
|---|---|
| Proteus vulgaris<br>Proteus mirabilis<br>Proteus morgani | } Proteus species |

Pseudomonas aeruginosa
Alcaligenes faecalis
Vibrio cholerae
Hemophilus-Bordetella group

| | |
|---|---|
| Hemophilus influenzae, | H. ducreyi<br>H. hemophilus<br>H. aegypticus<br>H. parainfluenzae |

Bordetella pertussis
Pasteurellae
Pasteurella pestis
Pasteurella tulareusis
Brucellae
Brucella melitensis
Brucella abortus
Brucella suis
Aerobic Spore-forming Bacilli
Bacillus anthracis
Bacillus subtilis -continued Bacillus megaterium
Bacillus cereus
Anaerobic Spore-forming Bacilli
Clostridium botulinum
Clostridium tetani
Clostridium perfringens
Clostridium novyi
Clostridium septicum
Clostridium histolyticum
Clostridium tertium
Clostridium bifermentans
Clostridium sporogenes
Mycobacteria
Mycobacterium tuberculosis hominis
Mycobacterium bovis
Mycobacterium avium
Mycobacterium leprae
Mycobacterium paratuberculosis
Actinomycetes (fungus-like bacteria)
Actinomyces israelii
Actinomyces bovis
Actinomyces naeslundii
Nocardia asteroides
Nocardia brasiliensis
The Spirochetes
Treponema pallidum    Spirillum minus
Treponema pertenue    Streptobacillus moniliformis
Treponema carateum
Borrelia recurrentis
Leptospira icterohemorrhagiae
Leptospira canicola
Mycoplasmas
Mycoplasma pneumoniae
Other pathogens
Listeria monocytogenes
Erysipelothrix rhusiopathiae
Streptobacillus moniliformis
Donvania granulomatis
Bartonella bacilliformis
Rickettsiae (bacteria-like parasites)
Rickettsia prowazekii
Rickettsia mooseri
Rickettsia rickettsii
Rickettsia conori
Rickettsia australis
Rickettsia sibiricus
Rickettsia akari
Rickettsia tsutsugamushi
Rickettsia burnetii
Rickettsia quintana
Chlamydia (unclassifiable parasites bacterial/viral)
Chlamydia agents (naming uncertain)
Fungi
Cryptococcus neoformans
Blastomyces dermatidis
Histoplasma capsulatum
Coccidioides immitis
Paracoccidioides brasiliensis
Candida albicans
Aspergillus fumigatus
Mucor corymbifer (Absidia corymbifera)
Rhizopus oryzae       ⎫
Rhizopus arrhizus     ⎬ Phycomycetes
Rhizopus nigricans    ⎭
Sporotrichum schenkii
Fonsecaea pedrosoi
Fonsecaea compacta
Fonsecaea dermatidis
Cladosporium carrionii
Phialophora verrucosa
Aspergillus nidulans
Madurella mycetomi
Madurella grisea
Allescheria boydii
Phialophora jeanselmei
Microsporum gypseum
Trichophyton mentagrophytes
Keratinomyces ajelloi
Microsporum canis -continued Trichophyton rubrum
Microsporum andouini
Viruses
Adenoviruses
Herpes Viruses
Herpes simplex
Varicella (Chicken pox)
Herpes Zoster (Shingles)
Virus B
Cytomegalovirus
Pox Viruses
Variola (smallpox)
Vaccinia
Poxvirus bovis
Paravaccinia
Molluscum contagiosum
Picornaviruses
Poliovirus
Coxsackievirus
Echoviruses
Rhinoviruses
Myxoviruses
Influenza (A, B, and C)
Parainfluenza (1–4)
Mumps Virus
Newcastle Disease Virus
Measles Virus
Rinderpest Virus
Canine Distemper Virus
Respiratory Syncytial Virus
Rubella Virus
Arboviruses
Eastern Equine Encephalitis Virus
Western Equine Encephalitis Virus
Sindbis Virus
Chikungunya Virus
Semliki Forest Virus
Mayora Virus
St. Louis Encephalitis Virus
California Encephalitis Virus
Colorado Tick Fever Virus
Yellow Fever Virus
Dengue Virus
Reoviruses
Reovirus Types 1–3
Hepatitis
Hepatitis A Virus
Hepatitis B Virus
Tumor Viruses
Rauscher Leukemia Virus
Gross Virus
Maloney Leukemia Virus The monoepitopic ligand analytes will generally be from about 100 to 2,000 molecular weight, more usually from 125 to 1,000 molecular weight. The analytes of interest include drugs, metabolites, pesticides, pollutants, and the like. Included among drugs of interest are the alkaloids. Among the alkaloids are morphine alkaloids, which includes morphine, codeine, heroin, dextromethorphan, their derivatives and metabolites; cocaine alkaloids, which includes cocaine and benzoyl ecgonine, their derivatives and metabolites; ergot alkaloids, which includes the diethylamide of lysergic acid; steroid alkaloids; iminazoyl alkaloids; quinazoline alkaloids, isoquinoline alkaloids; quinoline alkaloids; which includes quinine and quinidine; diterpene alkaloids; their derivatives and metabolites.

The next group of drugs includes steroids, which includes the estrogens, gestogens, androgens, andrenocortical steroids, bile acids, cardiotonic glycosides and aglycones, which includes digoxin and digoxigenin, saponins and sapogenins, their derivatives and metabolites. Also included are the steriod mimetic substances, such as diethylstilbestrol.

The next group of drugs is lactams having from 5 to 6 annular members, which include the barbiturates, e.g. phenobarbital and secobarbital, diphenylhydantonin, primidone, ethosuximide, and their metabolites.

The next group of drugs is aminoalkylbenzenes, with alkyl of from 2 to 3 carbon atoms, which includes the amphetamines, catecholamines, which includes ephedrine, L-dopa, epinephrine, narceine, papaverine, their metabolites.

The next group of drugs is aminoalkylbenzenes, with alkyl of from 2 to 3 carbon atoms, which includes ephedrine, L-dopa, epinephrine, narceine, papverine, their metabolites and derivatives.

The next group of drugs is benzheterocyclics which include oxazepam, chlorpromazine, tegretol, imipramine, their derivatives and metabolites, the heterocyclic rings being azepines, diazepines and phenothiazines.

The next group of drugs is purines, which includes theophylline, caffeine, their metabolites and derivatives.

The next group of drugs includes those derived from marijuana, which includes cannabinol and tetrahydrocannabinol.

The next group of drugs includes the vitamins such as A, B complex, e.g. $B_{12}$, C, D, E and K, folic acid, thiamine.

The next group of drugs is prostaglandins, which differ by the degree and sites of hydroxylation and unsaturation.

The next group of drugs is antibiotics, which include penicillin, chloromycetin, actinomycetin, tetracycline, terramycin, their metabolites and derivatives.

The next group of drugs is the nucleosides and nucleotides, which include ATP, NAD, FMN, adenosine, guanosine, thymidine, and cytidine with their appropriate sugar and phosphate substituents.

The next group of drugs is miscellaneous individual drugs which include methadone, meprobamate, serotonin, meperidine, amitriptyline, nortriptyline, lidocaine, procaineamide, acetylprocaineamide, propranolol, griseofulvin, valproic acid, butyrophenones, antihistamines, anticholinergic drugs, such as atropine, their metabolites and derivatives.

The next group of compounds is amino acids and small peptides which include polyiodothyronines e.g. thyroxine, and triiodothyronine, oxytocin, ACTH, angiotensin, met-and leu-enkephalin their metabolites and derivatives.

Metabolites related to diseased states include spermine, galactose, phenylpyruvic acid, and porphyrin Type 1.

The next group of drugs is aminoglycosides, such as gentamicin, kanamicin, tobramycin, and amikacin.

Among pesticides of interest are polyhalogenated biphenyls, phosphate esters, thiophosphates, carbamates, polyhalogenated sulfenamides, their metabolites and derivatives.

For receptor analytes, the molecular weights will generally range from 10,000 to $2 \times 10^6$, more usually from 10,000 to $10^6$. For immunoglobulins, IgA, IgG, IgE and IgM, the molecular weights will generally vary from about 160,000 to about $10^6$. Enzymes will normally range from about 10,000 to 6000,000 in molecular weight. Natural receptors vary widely, generally being at least about 25,000 molecular weight and may be $10^6$ or higher molecular weight, including such materials as avidin, thyroxine binding globulin, thyroxine binding prealbumin, transcortin, etc.

Signal Producing System

The signal producing system will have at least two members and will provide a detectible signal in the assay medium. The level of the observed signal will be influenced by the degree of interaction between the label of the labeled ligand and the macromolecular reagent as affected by matrix formation by binding of antireceptor to ligand receptor bound to labelled ligand. Desirably, the signal producing system should provide for several measurable events in response to each binding between ligand and antiligand (amplification).

The signal producing systems of primary interest are those involving catalysts, either enzymatic or nonenzymatic, particularly enzymatic, or chromophores which absorb or emit light, particularly fluorescers and chemiluminescers, as well as combinations of the two types of systems.

The first type of system to be considered will be those involving enzymes.

Enzymes

The desirable enzymes will be those having a high turnover rate, which can be readily conjugated to a wide variety of ligands, which will be relatively insensitive to nonspecific interactions, will have a turnover rate subject to modulation by a macromolecular reagent, and will produce a product which is measurable, particularly by absorption or emission of electromagnetic radiation.

The following are categories of enzymes as set forth in accordance with the classification of the International Union of Biochemistry.

TABLE II

1. Oxiodoreductases
    1.1 Acting on the CH—OH group of donors
        1.1.1 With NAD or NADP as acceptor
        1.1.2 With a cytochrome as an acceptor
        1.1.3 With $O_2$ as acceptor
        1.1.99 With other acceptors
    1.2 Acting on the aldehyde or keto group of donors
        1.2.1 With NAD or NADP as acceptor
        1.2.2 With cytochrome as an acceptor
        1.2.3 With $O_2$ as acceptor
        1.2.4 With lipoate as acceptor
        1.2.99 With other acceptors
    1.3 Acting on the CH—CH group of donors
        1.3.1 With NAD or NADP as acceptors
        1.3.2 With a cytochrome as an acceptor
        1.3.3 With $O_2$ as acceptor
        1.3.99 With other acceptors
    1.4 Acting on the CH—$NH_2$ group of donors
        1.4.1 With NAD or NADP as acceptor
        1.4.3 With $O_2$ as acceptor
    1.5 Acting on the C—NH group of donors
        1.5.1 With NAD or NADP as acceptor
        1.5.3 With $O_2$ as acceptor
    1.6 Acting on reduced NAD or NADP as donor
        1.6.1 With NAD or NADP as acceptor
        1.6.2 With a cytochrome as an acceptor
        1.6.4 With a disulfide compound as acceptor
        1.6.5 With a quinone or related compound as acceptor
        1.6.6 With a nitrogeneous group as acceptor
        1.6.99 With other acceptors
    1.7 Acting on other nitrogeneous compounds as donors
        1.7.3 With $O_2$ as acceptor
        1.7.99 With other acceptors
    1.8 Acting on sulfur groups of donors
        1.8.1 With NAD or NADP as acceptor
        1.8.3 With $O_2$ as acceptor
        1.8.4 With a disulfide compound as acceptor TABLE II-continued

| | | |
|---|---|---|
| | 1.8.5 | With a quinone or related compound as acceptor |
| | 1.8.6 | With nitrogeneous group as acceptor |
| 1.9 | Acting on heme groups of donors | |
| | 1.9.3 | With $O_2$ as acceptor |
| | 1.9.6 | With a nitrogeneous group as acceptor |
| 1.10 | Acting on diphenols and related substances as donors | |
| | 1.10.3 | With $O_2$ as acceptors |
| 1.11 | Acting on $H_2O_2$ as acceptor | |
| 1.12 | Acting on hydrogen as donor | |
| 1.13 | Acting on single donors with incorporation of oxygen (oxygenases) | |
| 1.14 | Acting on paired donors with incorporation of oxygen into one donor (hydroxylases) | |
| | 1.14.1 | Using reduced NAD or NADP as one donor |
| | 1.14.2 | Using ascorbate as one donor |
| | 1.14.3 | Using reduced pteridine as one donor |
| 2. Transferases | | |
| 2.1 | Transferring one-carbon groups | |
| | 2.1.1 | Methyltransferases |
| | 2.1.2 | Hydroxymethyl-, formyl- and related transferases |
| | 2.1.3 | Carboxyl- and carbamoyltransferases |
| | 2.1.4 | Amidinotransferases |
| 2.2 | Transferring aldehydic or ketonic residues | |
| 2.3 | Acyltransferases | |
| | 2.3.1 | Acyltransferases |
| | 2.3.2 | Aminoacyltransferases |
| 2.4 | Glycosyltransferases | |
| | 2.4.1 | Hexosyltransferases |
| | 2.4.2 | Pentosyltransferases |
| 2.5 | Transferring alkyl or related groups | |
| 2.6 | Transferring nitrogenous groups | |
| | 2.6.1 | Aminotransferases |
| | 2.6.3 | Oximinotransferases |
| 2.7 | Transferring phosphorus-containing groups | |
| | 2.7.1 | Phosphotransferases with an alcohol group as acceptor |
| | 2.7.2 | Phosphotransferases with a carboxyl group as acceptor |
| | 2.7.3 | Phosphotransferases with a nitrogeneous group as acceptor |
| | 2.7.4 | Phosphotransferases with a phospho-group as acceptor |
| | 2.7.5 | Phosphotransferases, apparently intromolecular |
| | 2.7.6 | Pyrophosphotransferases |
| | 2.7.7 | Nucleotidyltransferases |
| | 2.7.8 | Transferases for other substituted phospho-groups |
| 2.8 | Transferring sulfur-containing groups | |
| | 2.8.1 | Sulfurtransferases |
| | 2.8.2 | Sulfotransferases |
| | 2.8.3 | CoA-transferases |
| 3. Hydrolases | | |
| 3.1 | Acting on ester bonds | |
| | 3.1.1 | Carboxylic ester hydrolases |
| | 3.1.2 | Thiolester hydrolases |
| | 3.1.3 | Phosphoric monoester hydrolases |
| | 3.1.4 | Phosphoric diester hydrolases |
| | 3.1.5 | Triphosphoric monoester hydrolases |
| | 3.1.6 | Sulfuric ester hydrolases |
| 3.2 | Acting on glycosly compounds | |
| | 3.2.1 | Glycoside hydrolases |
| | 3.2.2 | Hydrolyzing N-glycosyl compounds |
| | 3.2.3 | Hydrolizing S-glycosyl compounds |
| 3.3 | Acting on ether bonds | |
| | 3.3.1 | Thioether hydrolases |
| 3.4 | Acting on peptide bonds (peptide hydrolases) | |
| | 3.4.1 | α-Aminoacyl-peptide hydrolases |
| | 3.4.2 | Peptidyl-aminoacid hydrolases |
| | 3.4.3 | Dipeptide hydrolases |
| | 3.4.4 | Peptidyl-peptide hydrolases |
| 3.5 | Acting on C—N bonds other than peptide bonds | |
| | 3.5.1 | In linear amides |
| | 3.5.2 | In cyclic amides |
| | 3.5.3 | In linear amidines |
| | 3.5.4 | In cyclic amidines |
| | 3.5.5 | In cyanides |
| | 3.5.99 | In other compounds |

TABLE II-continued

| | | |
|---|---|---|
| 3.6 | Acting on acid-anhydride bonds | |
| | 3.6.1 | In phosphoryl-containing anhydrides |
| 3.7 | Acting on C—C bonds | |
| | 3.7.1 | In ketonic substances |
| 3.8 | Acting on halide bonds | |
| | 3.8.1 | In C-halide compounds |
| | 3.8.2 | In P-halide compounds |
| 3.9 | Acting on P—N bonds | |
| 4. Lyases | | |
| 4.1 | Carbon-carbon lyases | |
| | 4.1.1 | Carboxy-lyases |
| | 4.1.2 | Aldehyde-lyases |
| | 4.1.3 | Ketoacid-lyases |
| 4.2 | Carbon-oxygen lyases | |
| | 4.2.1 | Hydro-lyases |
| | 4.2.99 | Other carbon-oxygen lyases |
| 4.3 | Carbon-nitrogen lyases | |
| | 4.3.1 | Ammonia-lyases |
| | 4.3.2 | Amidine-lyases |
| 4.4 | Carbon-sulfur lyases | |
| 4.5 | Carbon-halide lyases | |
| 4.99 | Other lyases | |
| 5. Isomerases | | |
| 5.1 | Racemases and epimerases | |
| | 5.1.1 | Acting on amino acids and derivatives |
| | 5.1.2 | Acting on hydroxy acids and derivatives |
| | 5.1.3 | Acting on carbohydrates and derivatives |
| | 5.1.99 | Acting on other compounds |
| 5.2 | Cis-trans isomerases | |
| 5.3 | Intramolecular oxidoreductases | |
| | 5.3.1 | Interconverting aldoses and ketoses |
| | 5.3.2 | Interconverting keto and enol groups |
| | 5.3.3 | Transposing C=C bonds |
| 5.4 | Intramolecular transferases | |
| | 5.4.1 | Transferring acyl groups |
| | 5.4.2 | Transferring phosphoryl groups |
| | 5.4.99 | Transferring other groups |
| 5.5 | Intramolecular lyases | |
| 5.99 | Other isomerases | |
| 6 Ligases or Synthetases | | |
| 6.1 | Forming C—O bonds | |
| | 6.1.1 | Aminoacid—RNA ligases |
| 6.2 | Forming C—S bonds | |
| | 6.2.1 | Acid-thiol ligases |
| 6.3 | Forming C—N bonds | |
| | 6.3.1 | Acid-ammonia ligases (amide synthetases) |
| | 6.3.2 | Acid-aminoacid ligases (peptide synthetases) |
| | 6.3.3 | Cylo-ligases |
| | 6.3.4 | Other C—N ligases |
| | 6.3.5 | C—N ligases with glutamine as N-donor |
| 6.4 | Forming C—C bonds | |

Of particular interest will be enzymes which are in Class 1. Oxidoreductases and Class 3 hyrdolases, although enzymes of Class 2, Transferases, Class 4 Lyases and Class 5, Isomerases, can also be of interest in particular situations.

The following table has specific subclasses of enzymes and specific enzymes within the subclass which are of particular interest. Among the oxidoreductases, those involving NAD or NADP, oxygen or hydrogen peroxide are of particular interest. Among the hydrolases, those involving phosphate and glycosides are of particular interest.

TABLE III

1. Oxidoreductases
   1.1  Acting on the CH—OH group of donors
       1.1.1  With NAD or NADP as acceptor
           1. alcohol dehydrogenase
           6. glycerol dehydrogenase
           27. lactate dehydrogenase

TABLE III-continued

|  |  |  |
|---|---|---|
|  | 37. malate dehydrogenase |  |
|  | 49. glucose-6-phosphate dehydrogenase |  |
| 1.1.3 | With $O_2$ as acceptor |  |
|  | 4. glucose oxidase |  |
|  | galactose oxidase |  |
| 1.2 | Acting on the aldehyde or keto group of donors |  |
| 1.2.1 | With NAD or NADP as acceptor |  |
|  | 12. glyceraldehyde-3-phosphate dehydrogenase |  |
| 1.2.3 | With $O_2$ as acceptor |  |
|  | 2. xanthine oxidase |  |
|  | luciferase |  |
| 1.4 | Acting on the CH—$NH_2$ group of donors |  |
| 1.4.3 | With $O_2$ as acceptor |  |
|  | 2. L-amino acid oxidase |  |
|  | 3. D-amino acid oxidase |  |
| 1.6 | Acting on reduced NAD or NADP as donor |  |
| 1.6.99 | With other acceptors |  |
|  | diaphorase |  |
| 1.7 | Acting on other nitrogenous compounds as donors |  |
| 1.7.3 | With $O_2$ as acceptor |  |
|  | 3. Uricase |  |
| 1.11 | Acting on $H_2O_2$ as acceptor |  |
| 1.11.1 |  |  |
|  | 6. catalase |  |
|  | 7. peroxidase |  |
| 2. Transferases |  |  |
| 2.7 | Transferring phosphorus-containing groups |  |
| 2.7.1 | Phosphotransferases with CH—OH as acceptor |  |
|  | 1. hexokinase |  |
|  | 2. glucokinase |  |
|  | 15. ribokinase |  |
|  | 28. triokinase |  |
|  | 40. pyruvate kinase |  |
| 2.7.5 | 1. phosphoglucomutase |  |
| 3. Hydrolases |  |  |
| 3.1 | Acting on ester bonds |  |
| 3.1.1 | Carboxylic ester hydrolases |  |
|  | 7. cholinesterase |  |
|  | 8. psuedo cholinesterase |  |
| 3.1.3 | Phosphoric monoester hydrolases |  |
|  | 1. alkaline phosphatase |  |
|  | 2. acid phosphatase |  |
|  | 9. glucose-6-phosphatase |  |
|  | 11. fructose diphosphatase |  |
| 3.1.4 | Phosphoric diester hydrolases |  |
|  | 1. phosphodiesterase |  |
|  | 3. phospholipase C |  |
| 3.2 | Acting on glycosyl compounds |  |
| 3.2.1 | Glycoside hydrolases |  |
|  | 1. alpha amylase |  |
|  | 2. beta amylase |  |
|  | 4. cellulase |  |
|  | 17. muramidase |  |
|  | 18. neuraminidase |  |
|  | 21. beta glucosidase |  |
|  | 23. beta galactosidase |  |
|  | 31. beta glucuronidase |  |
|  | 35. hyaluronidase |  |
| 3.2.2 | Hydrolyzing N-glysocyl compounds |  |
|  | 5. DPNase |  |
| 4. lyases |  |  |
| 4.1 | Carbon-carbon lyases |  |
| 4.1.2 | Aldehyde lyases |  |
|  | 13. aldolyase |  |
| 4.2.1 | Hydro-lyases |  |
|  | 1. carbonic anhydrase |  |
| 5. Isomerase |  |  |
| 5.4 | Intramolecular transferases |  |
| 5.4.2 | Transferring phosphoryl group |  |
|  | triose phosphate isomerase |  |

For the most part single enzymes will be employed which will be inhibited from interacting with the macromolecular reagent, which will normally involve an enzyme inhibitor, an enzyme substrate or cofactor. Alternatively, a combination of enzymes may be used where the product of one enzyme is the substrate of the other, where the result of the two reactions is to produce the detectible signal. By virtue of the extension of the reticulated microstructure of the matrix, and the enhanced proximity of the two enzymes to each other within the matrix, the presence of the antireceptor will enhance the signal.

Various combinations may be employed, such as combinations employing oxidoreductases which are dependent on NAD or NADP, where the formation of either the reduced from or oxidized form of the cofactor may be followed. The oxidoreductases may be employed in combination with transferases, hydrolases, lyases, or isomerases, particularly involving phosphate esters or glycosidyl ethers. Other combinations include the formation of hydrogen peroxide followed by the use of the hydrogen peroxide by the second enzyme to provide chemiluminescence. Alternatively, by providing for proximity between the enzyme and fluorescer, the chemiluminescer material may serve as a donor to the fluorescer and the fluorescence of the fluorescer observed. Various chromogens may be linked to groups which require initial modification, before removal of the group from the chromogen to provide for an active chromogen. Particularly useful are hydrolase esters for this purpose.

The following tables are illustrative of some of the combinations indicated above.

TABLE IV

|  | Category I.U.B. | Enzyme | Exemplary Reaction |
|---|---|---|---|
| 1. | 2.7.1 | Hexokinase | glucose + ATP → glucose-6-phosphate + ADP |
|  | 1.1.1 | glucose-6-phosphate dehydrogenase | glucose-6-phosphate + NADP → 6-P-glucuronate + NADPH |
| 2. | 4.1.2 | aldolase | fructose-1,6-dip → dihydroxyacetone-P + glyceraldehyde-3-P |
|  | 1.2.1 | glyceraldehyde-P dehydrogenase | glyceraldehyde-3-P + NAD → 3-phosphoglycerate + NADH |
| 3. | 3.1.3 | alkaline phosphatase | dihydroxyacetone diphosphate → dihydroxyacetone phosphate |
|  | 1.2.1 | glycerol-3-P dehydrogenase | dihydroxyacetone phosphate + NADH → glyceryl phosphate + NAD |
| 4. | 2.7.1 | pyruvate kinase | phosphoenol pyruvate + ADP → pyruvate + ATP |
|  | 1.1.1 | lactate dehydrogenase | pyruvate + NADH → lactate + NAD |
| 5. | 3.1.3 | alkaline phosphatase | 1,6-glucosyl diphosphate → G-6-P |
|  | 1.1.1 | glucose-6-phosphate dehydrogenase | G-6-P + NADP → 6-P-glucuronate + NADPH |
| 6. | 5.4.2 | triose phosphate isomerase | glyceraldehyde-3-P → dihydroxyacetone phosphate |
|  | 1.2.1 | α-glycerol-3-P dehydrogenase | dihydroxyacetone phosphate + NADH → glyceryl phosphate + NAD |
| 7. | 3.1.3 | alkaline phosphatase | D-sorbitol phosphate → D-sorbital |

TABLE IV-continued

| | Category I.U.B. | Enzyme | Exemplary Reaction |
|---|---|---|---|
| | 1.1.1 | α-D-hexitol dehydrogenase | D-sorbital + NADP → α-D-glucopyranose + NADPH |
| 8 | 5.4.2 | phosphoglucomutase | α-glucose-1-phosphate → glucose-6-phosphate |
| | 1.1.1 | glucose-6-phosphate dehydrogenase | glucose-6-phosphate + NAD → 6-P-glucuronate + NADH |
| 9. | 4.1.1 | pyruvate decarboxylase | pyruvate → acetaldehyde |
| | 1.1.1 | alcohol dehydrogenase | acetaldehyde + NADH → ethanol + NAD |
| 10. | 4.2.1 | fumarase | fumarate → malate |
| | 1.1.1 | malate dehydrogenase | malate + NAD → oxalacetate + NADH |
| 11. | 4.2.1 | aconitase | cis-aconitate → isocitrate |
| | 1.1.1 | isocitrate dehydrogenase | isocitrate + NAD → α-oxoglutarate + NADH |

Another combination of enzymes involves the formation of hydrogen peroxide, where the resulting catalyzed reaction by peroxidase of the hydrogen peroxide with a chemiluminescent material, e.g. luminol, produces light. The chemiluminescent compound may be the direct source of light or may be allowed to interact with an acceptor, such as 9,10-dibromoanthracene, which will then emit light. Alternatively one can provide a wide variety of dye precursors which will undergo enzymatically catalyzed reactions with hydrogen peroxide to produce the colored form which can be detected.

The following table indicates a number of these reactions in which both enzymes are signal labels.

TABLE V

| | Enzyme Category | Enzyme | Exemplary Reaction |
|---|---|---|---|
| 1. | 1.1.3 | glucose oxidase | glucose + $O_2$ → glucuronate + $H_2O_2$ |
| | 1.11.1 | peroxidase | $H_2O_2$ + luminol → products + hν |
| 2. | 1.7.3 | uricase | urate + $O_2$ → allantoin + $H_2O_2$ |
| | 1.11.1 | peroxidase | $H_2O_2$ + O-dianisidine → dye |
| 3. | 1.4.3 | D-amino acid oxidase | D-alanine + $O_2$ → pyruvate + $H_2O_2$ |
| | 1.11.1 | catalase | $H_2O_2$ + $Fe(CN)_6^{-4}$ → $Fe(CN)_6^{-3}$ |
| 4. | 1.2.3 | xanthine oxidase | xanthine + $O_2$ → uric acid + $H_2O_2$ |
| | 1.11.1 | cytochrome C oxidase | $H_2O_2$ + pyrogallol → hydroxyquinone |

A wide variety of non-enzymatic catalysts are described in U.S. Patent Application Ser. No. 815,636, the appropriate portions of which are incorporated herein by reference. The non-enzymatic catalysts employ as their reactants a first compound which reacts by one electron transfer and a second compound which reacts by a two electron transfer, where the two reactants are capable of reacting with each other slowly, if at all, in the absence of the catalyst. By providing for one of the reactants as a macromolecular reagent, the signal observed will be affected by the degree of matrix formation.

Besides catalysts as labels, one can also have chromogenic materials as labels, particularly compounds which fluoresce or chemiluminesce. By bonding the chromogenic label to the ligand, when the labeled ligand is in the matrix, interaction with a macromolecular reagent can be inhibited. Both fluorescent and chemiluminescent molecules can find employment.

Fluorescers of interest fall into a variety of categories having certain primary functionalities. These primary functionalities include 1- and 2-aminonaphthalene, p,p'-diaminostilbenes, pyrenes, quaternary phenanthridine salts, 9-aminoacridines, p,p-diaminobenzophenone imines, anthracenes, oxacarbocyanine, merocyanine, 3-aminoequilenin, perylene, bis-benzoxazole, bis-p-oxazolyl benzene, 1,2-benzophenazin, retinol, bis-3-aminopyridinium salts, hellebrigenin, tetracycline, sterophenol, benzimodazoylphenylamine, 2-oxo-3-chromen, indole, xanthene, 7-hydroxycoumarin, phenoxazine, salicylate, strophanthidin, porphyrins, triarylmethanes, flavin, and rare earth chelates.

Individual fluorescent compounds which have functionalities for linking or can be modified to incorporate such functionalities include dansyl chloride, fluoresceins such as 3,6-dihydroxy-9-phenylxanthhydrol, rhodamineisothiocyanate, N-phenyl 1-amino-8-sulfonatonaphthalene, N-phenyl 2-amino-6-sulfonatonaphthalene, 4-acetamido-4-isothiocyanato-stilbene-2,2'-disulfonic acid, pyrene-3-sulfonic acid, 2-toluidinonaphthalene-6-sulfonate, N-phenyl, N-methyl 2-aminonaphthalene-6-sulfonate, ethidium bromide, atebrine, auromine-0,2-(9'-anthroyl)palmitate, dansyl phosphatidylethanolamine, N,N'-dioctadecyl oxacarbocyanine, N,N'-dihexyl oxacarbocyanine, mercocyanine, 4-(3'-pyrenyl)butyrate, d-3-aminodesoxyequilenin, 12-(9'-anthroyl)stearate, 2-methylanthracene, 9-vinylanthracene, 2,2'-(vinylene-p-phenylene)bis-benzoxazole, p-bis[2-(4-methyl-5-phenyloxazolyl)]benzene, 6-dimethylamino-1,2-benzophenazin, retinol, bis(3'-aminopyridinium) 1,10-decandiyl diiodide, sulfonaphthyl hydrazone of hellebrigenin, chlortetracycline, N-(7-dimethylamino-4-methyl-2-oxo-3-chromenyl)maleimide, N-[p-(2-benzimidazoyl)-phenyl]maleimide, N-(4-fluoranthyl) maleimide, bis(homovanillic acid), resazarin, 4-chloro-7-nitro-2.1.3-benzooxadiazole, merocyanine, 540, resorufin, rose bengal, and 2,4-diphenyl-3(2H)-furanone.

It should be noted that the absorption and emission characteristics of the bound dye may differ from the unbound dye. Therefore, when referring to the various wavelength ranges and characteristics of the dyes, it is intended to indicate the dyes as employed and not the dye which is unconjugated and characterized in an arbitrary solvent.

An alternative source of light as a detectible signal is a chemiluminescent source. The chemiluminescent source involves a compound which becomes electronically excited by a chemical reaction and may then emit light which serves as the detectible signal or donates energy to a fluorescent acceptor.

A diverse number of families of compounds have been found to provide chemiluminescence under a variety of conditions. One family of compounds is 2,3-dihydro-1,4-phthalazinedione. The most popular compound is luminol, which is the 5-amino compound. Other members of the family include the 5-amino-6,7,8-trimethoxy- and the dimethylamino-[ca/benz]analog. These compounds can be made to luminesce with alkaline hydrogen peroxide or calcium hypochlorite and base. Another family of compounds is the 2,4,5-triphenylimidazoles, with lophine as the common name for the parent product. Chemiluminescent analogs include para-dimethylamino and -methoxy substituents.

Instead of having the enzyme as a label, various enzymes may be employed as the macromolecular reagent, where a substrate of cofactor is the label. This technique is described in copending application Ser. No. 751,504, filed Dec. 17, 1976, which relevant disclosure is incorporated herein by reference. Either large enzymes (>30,000 mn) are employed or a plurality of enzymes may be joined to provide the macromolecular reagent.

The label may interact with the enzyme in two ways. A bond may be made or broken, where the signal producing portion of the label remains bound to the ligand. For example, a cofactor may be the label which binds to the apoenzyme to provide the holoenzyme. Alternatively, a chromophore e.g. fluorophore, may be substituted by an enzymatically labile bond, where the substituted chromophore does not give the desired detectable signal, while the unsubstituted chromophore does.

The second way is where the label is bonded to the ligand by an enzymatically labile bond, with the label giving the desired signal only when free from the ligand. Illustrative of such situation would be a chromophore which is inactive when joined to the ligand and active when free. Similarly, a cofactor, such as NAD or FMN, might be employed.

However, while the aforementioned labels will be more commonly employed, other types of labels may also find use, such as stable free radicals, including their creation and destruction, labels for potentiometric determination, and the like.

Macromolecular reagent

The macromolecular reagent has a molecular weight of at least about $1 \times 10^4$, preferably at least about $5 \times 10^4$, and more preferably at least about $1 \times 10^5$. The macromolecular reagent may be an individual compound, or a combination of individual compounds, which may be covalently or noncovalently linked, either through linking groups or by conjugation to a hub nucleus.

Various macromolecular compounds can be employed as the macromolecular reagent, particularly those that are polyvalent i.e. have two or more active sites and act by binding non-covalently to the labels. Receptors, particularly antibodies, can find use, which bind to the label (antilabel) which results in a change in the signal producing capability of the label. The receptor as the macromolecular reagent may be conjugated or unconjugated to other molecules.

Where an enzyme is the label, antienzyme may be employed, where the antienzyme is capable of substantially reducing the enzymatic activity of the enzyme. Alternatively, a second enzyme may be conjugated to the antienzyme, where the antienzyme does not have a significant inhibitory effect on the enzyme label. In this instance, one would have the product of one of the enzymes as the substrate of the other enzyme, so that the close spatial proximity of the two enzymes would provide for enhanced production of the product of the second enzyme, which could serve as the source of the detectible signal. Where a chromogen is employed, the binding of antichromogen to the chromogen label could afford a change in its absorption characteristics, could inhibit fluorescence of a fluorescer, or inhibit chemiluminescence of a chemiluminescer. In addition, a molecule capable of quenching the fluorescence or chemiluminescence could be bonded to the antichromogen.

Where an enzyme is the label, one could bond a plurality of small molecules to a hub nucleus, where the small molecules are enzyme inhibitors, enzyme substrates or enzyme cofactors. Depending upon the particular enzyme, a wide variety of different materials could be employed.

For example, with glycosidases, glycosidyl ethers may be employed, where the other member of the ether is a chromogen. By employing chromogens which have substantially different absorption characteristics when present as the ether or the hydroxyl e.g. phenolics, the rate of formation of the oxy compound can be followed. Alternatively, one could employ peroxidase and link a chemiluminescent compound to a hub nucleus, so that the enzyme label in the matrix is unable to react with the chemiluminescent compound. One could also employ cofactors, such as NAD, NADP, FMN, FAD, and the like.

By conjugating these compounds to a hub, enzymes in the matrix would be inactive, while any remaining enzyme in the bulk solution would be active. Furthermore, one could reverse the situation by employing enzyme inhibitors, either specific or nonspecific inhibitors, which would be bound to a hub nucleus. In this instance, the enzyme in the matrix would be protected from the inhibitor, while enzymes in the bulk solution would be deactivated. Various small compound inhibitors are known. These include fluorophosphonates for cholinesterase, and arylmercuric salts for active site sulfhydryl of hydrolases. See also copending application Ser. No. 815,632, filed July 14, 1977.

Labeled Ligand

The labeled ligand will involve conjugates of the label to any of the antigenic ligands described in the analyte section. Depending on the nature of the label, as well as the nature of the ligand, there can be a plurality of one or both in the labeled ligand.

For the most part, there will be a single type of label bonded to the ligand. That is, usually there will be a particular enzyme or particular chromogen bonded to the ligand.

The various hub nucleii which may be employed for joining the label and ligand have been described previously.

Kits

As a matter of convenience, the reagents can be provided as kits, where the reagents are in predetermined ratios, so as to substantially optimize the sensitivity of the assay in the range of interest. After reconstitution of dry reagents, in predetermined volumes, the concentration of the reagents will be at appropriate levels.

The reagents may be mixed with various ancillary materials, such as members of the signal producing system, stabilizers, proteins, buffers, and the like.

EXPERIMENTAL

The following examples are offered by way of illustration and not by way of limitation.

(All percents and parts not otherwise indicated are by weight, except for mixtures of liquids which are by volume. All temperatures not otherwise indicated are centigrade. The following abbreviations are employed: RT—Room temperature, HIgG—human γ-globulin; DMF—N,N-dimethyl formamide; PBS—phosphate buffered saline.

EXAMPLE 1

RADIOLABELING OF HUMAN IgG(HIgG)

To 49 mg of HIgG (15 mg/ml), in 50 mM sodium phosphate pH 8.0 was added 4.2 μmoles of $^{14}C$-succinic anhydride as a 0.07 M solution in acetone with rapid stirring at RT and the stirring continued for 30 min. To the mixture was then added hydroxylamine-HCl in water (0.75 M, adjusted to pH 8.0, with NaOH) to a final concentration of 0.25 M. After standing at RT for 30 min, the mixture was then dialyzed 5×0.5 l. of 50 mM phosphate, pH 7.0. The product was found to have 8.2 succinyl residues per protein molecule.

EXAMPLE 2

CONJUGATION OF RADIOLABELED HIgG WITH N-SUCCINIMIDYL m-N'-MALEIMIDYLBENZOATE (MBSE)

In 50 mM phosphate buffer, pH 7.0, was dissolved 33 mg of HIgG to provide a final concentration of 5 mg/ml. To the mixture was added with stirring 6.4 mmoles of MBSE as a 10 mg/ml solution in dry DMF with stirring under nitrogen. After stirring for 30 min at RT, the pH was adjusted to 5.0 with about 0.2 volumes of 1.0 M acetate. The products were eluted at 30 ml/hr from a column of Sephadex G25F (20×2.4 cm) equilibrated with 20 mM acetate, pH 5 containing 0.15 M NaCl (degassed and then nitrogen saturated). The protein emerged at the void volume. The product was found to have seven maleimide groups per mole.

EXAMPLE 3

CONJUGATION OF HIgG TO β-GALACTOSIDASE

The following is the general procedure employed. All the solutions used were carefully degassed and nitrogen saturated. The pH of the above reacted HIgG protein solutions after chromatography were adjusted to 7 by addition of 0.1 volume of 0.5 M phosphate, pH 7. Any volume adjustment necessary was made with 50 mM phosphate, pH 7 buffer. The enzyme was dissolved in 50 mM phosphate, pH 7 and added to the HIgG to initiate the conjugation which was carried out at RT under nitrogen. To terminate the reaction, cysteine (10 mM) was added to give a small excess over maleimide groups originally present. Before chromatography of the products, conjugates were concentrated under nitrogen pressure using an Amicon ultrafiltration cell with a PM-10 membrane. Any precipitated protein was removed by centrifugation.

Separation of unconjugated HIgG and enzyme from the conjugate was achieved by chromatography on a 82×1.5 cm Biogel A5M column using PBS containing 5 mM NaN$_3$+0.1 mM magnesium acetate as eluent. The flow rate was 4.8 ml/hr, with the conjugate emerging first fully resolved from unconjugated starting material.

TABLE VI

| Conjugate | β-galactosidase conc. μM | Reaction Time Hr. | Total IgG: β-galactosidase mole ratio | Conjugate HIgG: β-galactosidase mole ratio | % Activity of conjugate[a] |
|---|---|---|---|---|---|
| 0 | .24 | 1.5 | 11.3 | 2.8 | 100 |
| 2 | .21 | 21 | 17.5 | 4.3 | 95 |

[a]Determined by assay with o-nitrophenyl-β-galactoside. Protocol to be described.

EXAMPLE 4

CONJUGATION OF ONPG TO DEXTRAN T40 THROUGH N,N'-BIS-(3-AMINOPROPYL)-PIPERAZINE

A. 3-Hydroxy-4-nitrobenzoic acid (100.3 g, 95% pure, 0.53 mole) was added to methanol (1250 ml) to which had been added acetyl chloride (25 ml). The solid dissolved over a period of two days. After six days, the solution was filtered to remove undissolved impurities. The crude ester was obtained by evaporation of the solution. Several crops of crystals were taken, the last from a 50 ml volume. The combined crops were recrystalized from methanol (150 ml). Two crops of the ester as yellow-brown crystals, m.p. 89°–91°, (98.7 g, 0.50 mole) were obtained.

B. Acetobromogalactose (100.1 g, 95% pure, 0.23 mole) and methyl 3-hydroxy-4-nitrobenzoate (45.5 g, 0.23 mole) were dissolved in acetonitrile (600 ml). Silver oxide (30 g, 0.25 equiv.) was added to the stirred solution. The black solid gradually turned gray. After ten minutes, an additional portion of silver oxide (20 g, 0.17 equiv.) was added. Stirring was continued for an additional twenty minutes. The reaction mixture was filtered through a Celite pad to remove the silver salts. The filtrate was evaporated to give a crude brown crystaline mass (115 g). This material was recrystalized from ethanol (400 ml). Two crops of off-white crystals, m.p. 150°–152° (99.6 g, 0.19 mole, 83% yield) were obtained.

C. The tetracetate prepared above (B) (119 g, 0.226 mole) was added to methanol 1 l. The mixture was heated at 60° until the solid dissolved. Triethylamine (25 ml) was then added, and the solution was heated at 60° for an additional two hours. The crude solid product was obtained in several crops by evaporation of the solution, the final crop being taken from a 20 ml volume. The crude material was used in the next reaction without further purification.

D. The crude ester (prepared from 119 g of tetracetate in the preceding reaction) was added with stirring to 1 N NaOH 1.5 l. After 15 min, the ester had dissolved and hydrolyzed. The solution was neutralized with concentrated HCl to give a cloudy orange solution, pH 7.5. The solution was clarified by filtration, then acidified with 1 N HCl (250 ml) to give a light yellow solution, pH 3–3.5. The resulting acid precipitated and was collected by filtration. It was washed with water (20 ml) and methanol (50 ml). The crude acid was recrystalized from methanol (900 ml), giving silky white needles (34.7 g). The aqueous mother liquors were concentrated to an 800 ml volume and acidified to pH 2. An additional amount of the crude acid was obtained which was recrystalized from methanol (150 ml) to give needles (7.7 g). The total yield of purified acid was 42.4 g (123 mmoles), m.p. 172°–174°.

E. 3-β-Galactosyloxy-4-nitrobenzoic Acid (55.2 g, 0.160 mole), N-hydroxysuccinimide (20 g, 0.174 mole), and EDCI (35 g, 0.183 mole) were dissolved in DMF (200 ml). After two hours, the reaction was complete by TLC, (10–20% MeOH/CHCl₃) and showed some minor impurites in addition to the desired compound. The solution was used without further treatment.

F. Dextran T40 (101 g) was dissolved in 1.25 M aqueous sodium chloroacetate (500 ml). A 2.5 M aqueous solution of sodium hydroxide (500 ml) was added. The solution was heated at 80°–85° for 3 hr.

The reaction mixture was allowed to cool. Ethanol (1 l.) was added slowly to the stirred reaction mixture. The dextran began to precipitate after 350 ml had been added. Additional ethanol (2 l.) was added to ensure complete precipitation.

The precipitate separated as a gum. The supernatant was decanted easily. The dextran was purified by three additional precipitations. These were carried out in the following manner. The gum was dissolved in water (750 ml). Ethanol (3 l.) was then added slowly until a permanent cloudiness appeared in the solution, then more rapidly. The gummy precipitate of the dextran was then allowed to settle out overnight.

G. Carboxymethylated dextran T40 (as a gum, prepared from 100 g dextran T40) was dissolved in water (250 ml). A solution of N,N'-bis-(3-aminopropyl)piperazine (400 g, 2.0 mole) in hydrochloric acid (680 g of 8.52 mmole/g, 5.80 mole) was added. To the resulting solution was added EDCI (201 g, 1.05 mole) in water (250 ml). The reaction was stored at room temperature for 22 hrs. At the end of this period, ethanol (3 l.) was added. The dextran began to precipitate after 1.5 l. had been added. The precipitate was allowed to settle out overnight.

The aminodextran was purified by two additional precipitations. These were carried out as previously described. The final precipitation gave a milky suspension, which coagulated and settled out upon addition of a solution of lithium bromide (25 g) in ethanol (250 ml). The resulting gum was diluted in 1 l. and found to be 104 mM in amino broups by assay with trinitrobenzenesulfonic acid.

H. A solution of the aminodextran prepared above (G) (1 l. of 104 mM, 104 mmole) was treated with K₂HPO₄ (89 g, 0.5 mole) to give a solution buffered at pH 8–8.1 A DMF solution of the NHS ester (E) (160 mmole) was added slowly. The resulting solution was stored at room temperature for 24 hrs. The dextran was precipitated by the addition of ethanol (3 l.). Precipitation began after addition of 350 ml of the ethanol. The precipitate was allowed to settle out overnight.

The dextran was purified by two additional precipitations in the manner already described. The final gum was dissolved in water (1 l.). The solution was clarified by filtration first through a medium-porosity glass frit, and then through a 0.8μ Millipore filter.

The resulting solution was diluted to 2 l. A sample was diluted 1:121 and had $A_{320}=1.15$. Based on $E_{320}=2700$, the ONPG-group concentration was 52 mM.

The solution was preserved by addition of NaN₃ (0.65 g).

EXAMPLE 5

CONJUGATE OF FLUORESCEIN TO HUMAN IgG (HIgG)

HIgG (5 mg, Miles 64-156) is dialysed against 0.1 M Na₂CO₃, pH9.0, followed by combining the residue with 0.2 mg of fluorescein isothiocyanate dissolved in 50 μl DMF. After standing for 3 hrs in the dark at rt, the conjugate is chromatographed on a Sephadex G-25 column equilibrated with PBS, pH 7.8. The dye/protein ratio is determined by UV spectra with a Wells nomograph.

In order to demonstrate the subject invention, the following assays were performed. The assay buffer employed was PBS, 10 mM phosphate, 0.128 M NaCl, 5 mM sodium azide, 1 mg/ml RSA and 0.1 mM magnesium acetate. The conjugate 0 of Example 3 was dissolved in 50 μl. of the buffer to provide 7.1 μg β-galactosidase/ml. AntiHIgG (2.4 mg/ml) was serially diluted in the same buffer and a 25 μl aliquots combined with 50 μl aliquots of the enzyme conjugate and incubated for 1 hr at RT. To the mixture was then added 25 μl of serial dilutions of goat antibody to the antiHIgG (2.4 mg/ml) in the same buffer and the mixture incubated for an additional hour. The assay was then performed as follows. The dextran linked galactosidyl ether was dissolved in the subject buffer to provide a final concentration in the assay medium of 0.4 mM, where the assay sample had a total volume of 1 ml. Absorption was read at 420 nm employing a Stasar Spectrophotometer at 37° with the mixture aspirated into the Spectrophotometer and readings taken at 10 and 40 sec. The activity is expressed as a rate (ΔOD/min.). The following table indicates the results.

TABLE VII

| AntiHIgG dilution | AntiRIgG dilution | Rate ΔOD min⁻¹ᵃ | % Original Activity |
|---|---|---|---|
| ∞ | ∞ | .215 | 100 |
| 8 | ∞ | .048 | 22.3 |
| 256 | ∞ | .185 | 86.0 |
| 8 | 1 | .037 | 17.2 |
| 256 | 1 | .111 | 51.6 |
| 256 | 16 | .167 | 77..7 |
| 256 | 64 | .184 | 85.6 |

ᵃThe substrate was a conjugate to 40,000 m.w. Dextran prepared as described in Ex. 4 having a ONPG ratio of 1:5 sugar residue.

It is evident from the above results, that substantially enhanced inhibition of the enzyme results by providing for an antibody which binds to the antiligand, in this case antiHIgG.

Employing the above technique, an assay was performed for HIgG. A 25 μl portion of a serial dilution of HIgG solution (0.31 mg/ml) was mixed with 25 μl. of a serially diluted solution of rabbit antiHIgG in the same buffer and the mixture incubated for 1 hr at RT. To the mixture was then added Conjugate 2 of Example 3 in 50 μl (9 μg/ml β-galactosidase) and incubation continued for a further hour. To the mixture was then added goat anti(rabbit antiHIgG) (14.9 mg/ml) in 25 μl. and the mixture incubated for a third hour followed by assay with ONPG conjugate to Dextran of 40,000 m.w. The following table indicates the results.

TABLE VIII

| HIgG dilution ratio* | % enzyme activity at anti HIgG dilutions of | | |
|---|---|---|---|
| | 512 | 128 | 32 |
| 1:1 | 95 | 96 | 98 |
| 1:4 | 91 | 92 | 96 |
| 1:16 | 85 | 90 | 82 |
| 1:64 | 81 | 80 | 53 |
| 1:256 | 84 | 71 | 34 |
| 1:1024 | 79 | 62 | 33 |

*0.31mg/ml

The following assay employs a fluorescer as a label. The protocol was as follows. To 20 μl of $5 \times 10^{-10}$ M fluorescein-HIgG conjugate in 0.5 ml PBS, 2% PEG 6000, 0.05% NaN$_3$, pH7.8 buffer was added rabbit(antiHIgG) (20 μl, 9.1 mg protein/ml) and the mixture incubated at room temperature for 0.5 hr, followed by the addition of anti(rabbit(HIgG)) (Miles, Cat. No. 65-159, Lot S404, IgG fraction) (20 μl or 5 μl+15 μl buffer), a further incubation of 0.5 hr, followed by the addition of sheep antifluorescein (20 μl, 4 mg protein/ml), and after a twenty minute time interval, the fluorescence of the assay medium determined.

The following solutions were prepared and their fluorescence determined.

TABLE IX

| Assay Solution$^a$ | | | | % |
|---|---|---|---|---|
| F-HIgG | antiHIgG | antiRIgG | antiF | Fluorescence |
| + | — | — | — | 100 |
| + | + | 20μl | + | 78 |
| + | + | 5μl | + | 57 |
| + | + | — | + | 35 |
| + | — | — | + | 9 |

$^a$F-HIgG - fluorescein-human IgG
antiHIgG - rabbit antibodies to humanIgG
antiRIgG - sheep antibodies to rabbitIgG
antiF - antifluorescein
+ = present
— = absent The above results show that the presence of the antibody to the ligand antibody greatly enhances the protection of the fluorescein label from the antilabel where the fluorescein label is bound to the ligand through the intermediacy of the antiligand. In the present example, the fluorescein label is protected from the quenching antifluorescein when involved in a matrix involving ligand, antiligand and anti(antiligand).

It is evident from the above results, that the sensitivity of a variety of assays may be greatly enhanced by introducing a second antibody to enhance steric effects either by steric exclusion or by modulation, e.g. reduction, of the rates of diffusion. Thus, the originally observed effect in the absence of the second antibody is given a greater dynamic range so as to provide for more accurate results and greater sensitivity. In addition, because of the greater sensitivity, lower concentrations of various analytes may be determined.

Although the foregoing invention has been described in some detail by way of illustration and example for purposes of clarity of understanding, it will be obvious that certain changes and modifications may be practiced within the scope of the appended claims.

What is claimed is:

1. An assay method for determining the presence in a sample of an analyte which is a member of a specific binding pair consisting of ligand and its homologous receptor, antiligand;

said method employing:
(A) an aqueous medium;
(B) a signal producing system capable of producing a detectible signal and including at least two members, one of which is bonded to ligand and another of which is macromolecular and capable of modulating said signal when in spatial proximity to said member bonded to said ligand;
(C) labeled ligand, wherein ligand is conjugated to a member of said signal producing system and wherein said label is selected from fluorescers or enzymes;
(D) a polyvalent macromolecular member of said signal producing system having a molecular weight of at least about $1 \times 10^4$ daltons;
(E) antiligand, when ligand is the analyte;
(F) poly(ligand analog), when ligand has a single binding site to receptor; and
(G) anti(antiligand), which is a polyvalent receptor for antiligand wherein ligand, antiligand, and anti(antiligand) bind to form a matrix which results in said macromolecular member being enclosed in or excluded from said matrix, so as to have enhanced interaction with said labeled ligand or be prevented from interacting with said labeled ligand respectively;

said method comprising:
combining in an aqueous medium at a pH in the range of about 4 to 11 at a temperature in the range of about 10° to 50° C.:
(a) said sample;
(b) said labeled ligand;
(c) said macromolecular member;
(d) any remaining members of said signal producing system;
(e) anti(antiligand)
(f) antiligand, when ligand is the analyte; and
(g) poly(ligand analog), when haptenic ligand is the analyte; and after a sufficient time for antiligand and anti(antiligand) to bind to their homologous ligands determining the signal level from said signal producing system in said assay medium as compared to an assay medium having a known amount of analyte.

2. A method according to claim 1, wherein said aqueous medium is at a temperature in the range of about 15° to 40° C. and at a pH in the range of about 5 to 10.

3. A method according to claim 2, wherein said macromolecular member reduces said signal produced by said labeled ligand, and said method includes, combining in said assay medium, ligand analyte and antiligand and incubating, followed by adding anti(antiligand) and incubating, followed by adding said macromolecular member.

4. A method according to claim 3, wherein said macromolecular member is a receptor for label.

5. A method according to any of claims 2 to 4, wherein said label is an enzyme.

6. A method according to any of claims 2 to 4, wherein said label is a fluorescer.

7. An assay method for determining the presence in a sample of an antigenic ligand analyte, which is a member of a specific binding pair consisting of ligand and its homologous receptor, antiligand;

said method employing:
(A) an aqueous medium;
(B) a signal producing system capable of producing a detectible signal and including at least two members, one of which is an enzyme bonded to ligand and another of which is macromolecular and capable of modulating said signal when in spatial proximity to said enzyme member bonded to said ligand;

(C) labeled ligand wherein ligand is conjugated to said enzyme;

(D) a polyvalent macromolecular member of said signal producing system having a molecular weight of at least about $1 \times 10^4$ daltons;

(E) antiligand; and (F) anti(antiligand) which is a polyvalent receptor for anti(ligand), wherein the ligand, antiligand and anti(antiligand) bind to form a matrix which results in said macromolecular member being excluded from said matrix, so as to be prevented from interacting with said labeled ligand; said method comprising:

combining in an aqueous medium at a pH in the range of about 4 to 11 at a temperature in the range of about 10° to 50° C.:

(a) said sample;
(b) said labeled ligand;
(c) said macromolecular member;
(d) any remaining members of said signal producing system;
(e) anti(antiligand); and
(f) antiligand, when ligand is the analyte;

after a sufficient time for antiligand and anti(antiligand) to bind to their homologous ligands, determining the signal level from said signal producing system in said assay medium as compared to an assay medium having a known amount of analyte.

8. A method according to claim 7, wherein said ligand, labeled ligand, and antiligand are combined and incubated prior to introduction of said anti(antiligand) followed by addition of said anti(antiligand) and a second incubation.

9. A method according to any of claims 7 and 8, wherein said macromolecular member is a substrate for said enzyme.

10. A method according to claim 9, wherein said enzyme is beta-galactosidase and said substrate is a polysaccharide substituted ortho-nitrophenyl galactoside.

11. An assay method for determining the presence in a sample of an antigenic ligand analyte, which is a member of a specific binding pair consisting of ligand and its homologous receptor, antiligand;

said method employing:

(A) an aqueous medium;

(B) a signal producing system capable of producing a detectible signal and including at least two members, one of which is a fluorescer bonded to ligand and another of which is macromolecular and capable of modulating said signal when in spatial proximity to said fluorescer member bonded to said ligand;

(C) labeled ligand wherein ligand is conjugated to said fluorescer;

(D) a polyvalent macromolecular member of said signal producing system having a molecular weight of at least about $1 \times 10^4$ daltons;

(E) antiligand; and (F) anti(antiligand) which is a polyvalent receptor for anti(ligand), wherein the ligand, antiligand and anti(antiligand) bind to form a matrix which results in said macromolecular member being excluded from said matrix, so as to be prevented from interacting with said labeled ligand; said method comprising:

combining in an aqueous medium:

(a) said sample;
(b) said labeled ligand;
(c) said macromolecular member;
(d) any remaining members of said signal producing system;
(e) anti(antiligand); and
(f) antiligand, when ligand is the analyte;

after a sufficient time for antiligand and anti(antiligand) to bind to their homologous ligands, determining the signal level from said signal producing system in said assay medium as compared to an assay medium having a known amount of analyte.

12. An assay method according to claim 11, wherein said macromolecular member is antifluorescer.

13. A method according to claim 12, wherein said fluorescer is a fluorescein and said antifluorescer is an antibody to said fluorescein.

14. A method according to claim 11, wherein said fluorescer is a fluorescein.

15. An assay composition for use in the method of claim 1 comprising in combination in relative predetermined amounts to substantially optimize the signal level to variations in concentration of analyte, labeled ligand selected from enzyme labeled ligand or fluorescer labeled ligand, polyvalent macromolecules having a molecular weight of at least $1 \times 10^4$ daltons, and polyvalent anti(antiligand) which is capable of forming a matrix with ligand and antiligand which either encloses or excludes the marcromolecule, wherein the macromolecule and the label are members of a signal producing system and wherein when the analyte is a ligand, antiligand is included and when the analyte is haptenic ligand, a poly(ligand analog) is included.

16. An assay composition according to claim 15, wherein labeled ligand is enzyme bonded to ligand and said macromolecular member is an enzyme substrate.

17. An assay composition according to claim 15, wherein labeled ligand is fluorescer bonded to ligand and said macromolecular member is antifluorescer.

* * * * *